United States Patent
Schliephake et al.

(10) Patent No.: US 7,196,217 B2
(45) Date of Patent: Mar. 27, 2007

(54) OPERATION OF A CONTINUOUS HETEROGENEOUSLY CATALYZED GAS PHASE PARTIAL OXIDATION OF AT LEAST ONE ORGANIC COMPOUND

(75) Inventors: Volker Schliephake, Schifferstadt (DE); Ulrich Hammon, Mannheim (DE); Rolf-Dieter Becher, Mannheim (DE); Klaus Joachim Muller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 221 days.

(21) Appl. No.: 10/912,075

(22) Filed: Aug. 6, 2004

(65) Prior Publication Data

US 2005/0032918 A1    Feb. 10, 2005

Related U.S. Application Data

(60) Provisional application No. 60/530,616, filed on Dec. 19, 2003, provisional application No. 60/492,726, filed on Aug. 6, 2003.

(30) Foreign Application Priority Data

Aug. 6, 2003  (DE)  ................. 103 36 385
Dec. 19, 2003 (DE)  ................. 103 60 396

(51) Int. Cl.
  *C07C 51/235*  (2006.01)
  *C07C 51/16*   (2006.01)
(52) U.S. Cl. .................... 562/532; 562/545
(58) Field of Classification Search ............. None
  See application file for complete search history.

(56) References Cited

U.S. PATENT DOCUMENTS

| | | | |
|---|---|---|---|
| 3,119,837 A | 1/1964 | Kingsley et al. | |
| 3,562,185 A | 2/1971 | Friedrichsen et al. | |
| 3,799,866 A | 3/1974 | Felice et al. | |
| 3,956,377 A | 5/1976 | Dolhyj et al. | |
| 4,077,912 A | 3/1978 | Dolhyj et al. | |
| 4,408,079 A | 10/1983 | Merger et al. | |
| 4,496,770 A | 1/1985 | Duembgen et al. | |
| 5,173,468 A | 12/1992 | Boehning et al. | |
| 5,221,767 A | 6/1993 | Boehning et al. | |
| 5,231,226 A | 7/1993 | Hammon et al. | |
| 5,264,625 A | 11/1993 | Hammon et al. | |
| 5,637,222 A | 6/1997 | Herbst et al. | |
| 5,668,077 A | 9/1997 | Klopries et al. | |
| 5,734,068 A | 3/1998 | Klopries et al. | |
| 5,739,391 A | 4/1998 | Ruppel et al. | |
| 5,817,865 A | 10/1998 | Machhammer et al. | |
| 5,821,390 A | 10/1998 | Ruppel et al. | |
| 5,831,124 A | 11/1998 | Machhammer et al. | |
| 5,969,160 A * | 10/1999 | Lindstrom ................. 549/248 |
| 6,166,248 A | 12/2000 | Heida et al. | |
| 6,348,638 B1 | 2/2002 | Schliephake et al. | |
| 6,395,936 B1 | 5/2002 | Arnold et al. | |
| 6,403,829 B1 | 6/2002 | Unverricht et al. | |
| 6,410,785 B1 | 6/2002 | Zehner et al. | |
| 6,413,379 B1 | 7/2002 | Machhammer et al. | |
| 6,525,217 B1 | 2/2003 | Unverricht et al. | |
| 6,646,161 B1 | 11/2003 | Eck et al. | |
| 6,781,017 B2 | 8/2004 | Machhammer et al. | |
| 2001/0007043 A1 | 7/2001 | Machhammer et al. | |
| 2003/0181761 A1 | 9/2003 | Unverricht et al. | |
| 2003/0187298 A1 | 10/2003 | Borgmeier et al. | |
| 2003/0187299 A1 | 10/2003 | Machhammer et al. | |
| 2004/0034249 A1 | 2/2004 | Arnold et al. | |
| 2004/0116730 A1 | 6/2004 | Schliephake et al. | |
| 2004/0181083 A1 | 9/2004 | Proll et al. | |
| 2004/0192964 A1 | 9/2004 | Petzoldt et al. | |
| 2004/0192965 A1 | 9/2004 | Petzoldt et al. | |

FOREIGN PATENT DOCUMENTS

| | | |
|---|---|---|
| DE | 1 254 137 | 11/1967 |
| DE | 1 642 921 | 5/1971 |
| DE | 2 159 346 | 6/1972 |
| DE | 2 106 796 | 8/1972 |
| DE | 2 351 151 | 4/1974 |
| DE | 25 26 238 | 1/1976 |
| DE | 40 22 212 | 1/1992 |
| DE | 41 32 263 | 4/1993 |
| DE | 41 32 684 | 4/1993 |
| DE | 43 11 608 | 12/1994 |
| DE | 44 31 949 | 3/1995 |
| DE | 44 31 957 | 3/1995 |
| DE | 195 01 325 | 7/1996 |
| DE | 196 06 877 | 8/1997 |
| DE | 196 31 645 | 2/1998 |
| DE | 197 40 253 | 3/1999 |

(Continued)

OTHER PUBLICATIONS

Perry, Perry's Chemical Engineer's Handbook, 5th Edition, 1984, McGraw-Hill, Inc., pp. 6-24 to 6-26, 20-83 to 20-89 and 20-97 to 20-104.*

*Primary Examiner*—Paul A. Zucker
(74) *Attorney, Agent, or Firm*—Oblon, Spivak, McClelland, Maier & Neustadt, P.C.

(57) ABSTRACT

Process for operating a continuous heterogeneously catalyzed gas phase partial oxidation of at least one organic compound using compressed air as the oxygen source which is filtered before its compression.

26 Claims, No Drawings

FOREIGN PATENT DOCUMENTS

| | | |
|---|---|---|
| DE | 199 02 562 | 7/2000 |
| DE | 199 10 506 | 9/2000 |
| DE | 199 10 508 | 9/2000 |
| DE | 199 27 624 | 12/2000 |
| DE | 199 48 241 | 4/2001 |
| DE | 199 48 248 | 4/2001 |
| DE | 100 28 582 | 12/2001 |
| DE | 101 31 297 | 1/2002 |
| DE | 100 46 672 | 3/2002 |
| DE | 100 46 928 | 4/2002 |
| DE | 100 46 957 | 4/2002 |
| DE | 103 13 210 | 3/2003 |
| DE | 103 13 213 | 3/2003 |
| DE | 103 13 214 | 10/2004 |
| EP | 0 058 927 | 9/1982 |
| EP | 0 092 097 | 10/1983 |
| EP | 0 372 972 | 6/1990 |
| EP | 0 529 853 | 3/1993 |
| EP | 0 608 838 | 8/1994 |
| EP | 0 695 736 | 2/1996 |
| EP | 0 700 714 | 3/1996 |
| EP | 0 700 893 | 3/1996 |
| EP | 0 778 255 | 6/1997 |
| EP | 0 784 046 | 7/1997 |
| EP | 0 982 287 | 3/2000 |
| EP | 0 982 289 | 3/2000 |
| EP | 0 990 636 | 4/2000 |
| EP | 1 041 062 | 10/2000 |
| EP | 1 090 684 | 4/2001 |
| EP | 1 106 598 | 6/2001 |
| EP | 1 180 508 | 2/2002 |
| GB | 1 291 354 | 10/1972 |
| GB | 1 369 639 | 10/1974 |
| GB | 1 464 198 | 2/1977 |
| WO | WO 89/07101 | 8/1989 |
| WO | WO 97/48669 | 12/1997 |
| WO | WO 00/53556 | 9/2000 |
| WO | WO 00/53557 | 9/2000 |
| WO | WO 00/53558 | 9/2000 |
| WO | WO 00/53559 | 9/2000 |
| WO | WO 01/96270 | 12/2001 |

* cited by examiner

OPERATION OF A CONTINUOUS HETEROGENEOUSLY CATALYZED GAS PHASE PARTIAL OXIDATION OF AT LEAST ONE ORGANIC COMPOUND

BACKGROUND OF THE INVENTION

1. Field of the Invention

The present invention relates to a process process for operating a continuous heterogeneously catalyzed gas phase partial oxidation of at least one organic compound in an oxidation reactor whose charging gas mixture, in addition to the at least one compound to be partially oxidized and molecular oxygen as the oxidant, comprises at least one diluent gas which is substantially inert under the conditions of the heterogeneously catalyzed gas phase partial oxidation, by using air, both as the oxygen source and the inert gas source for the charging gas composition, which has been compressed beforehand in a compressor from a low starting pressure to a higher final pressure.

2. Description of the Background

In this context, a complete oxidation of an organic compound with molecular oxygen means that the organic compound is converted under the reactive action of molecular oxygen in such a way that all of the carbon present in the organic compound is converted to oxides of carbon and all the hydrogen present in the organic compound is converted to oxides of hydrogen. All differing conversions of an organic compound with reactive action of molecular oxygen are grouped together here as partial oxidation of an organic compound. In other words, the term partial oxidation in this document is intended to refer especially also to partial ammoxidations, which are characterized by the organic compound being partially reactively converted in the presence of ammonia.

In particular, partial oxidations in this context are intended to refer to those conversions of organic compounds with the reactive action of molecular oxygen in which the organic compound to be partially oxidized, on completion of conversion, contains at least one more oxygen atom in chemically bonded form than before the partial oxidation was carried out.

In this context, diluent gases which behave substantially inertly under the conditions of the heterogeneously catalyzed gas phase partial oxidation are those diluent gases of whose constituents, under the conditions of the heterogeneously catalyzed gas phase partial oxidation, taking each constituent on its own, more than 95 mol %, preferably more than 99 mol %, remain unchanged.

It is common knowledge that heterogeneously catalyzed partial oxidation of various organic precursor compounds with molecular oxygen in the gas phase allows numerous basic chemicals to be obtained.

Examples include the conversion of xylene to phthalic anhydride, the conversion of propylene to acrolein and/or acrylic acid (cf., for example, DE-A 2351151), the conversion of tert-butanol, isobutene, isobutane, isobutyraldehyde or the methyl ether of tert-butanol to methacrylonitrile or to methacrolein and/or methacrylic acid (cf., for example, DE-A 2526238, EP-A 92097, EP-A 58927, DE-A 4132263, DE-A 4132684 and DE-A 4022212), the conversion of acrolein to acrylic acid, the conversion of methacrolein to methacrylic acid (cf., for example, DE-A 2526238), the conversion of butadiene to maleic anhydride (cf., for example, DE-A2106796 and DE-A 1624921), the conversion of n-butane to maleic anhydride (cf., for example, GB-A 1464198 and GB-A 1291354), the conversion of ethylene to ethylene oxide or of propylene to propylene oxide (cf., for example, DE-B 1254137, DE-A 2159346, EP-A 372972, WO 89/0710, DE-A 4311608 and Beyer, Lehrbuch der organischen Chemie [Textbook of Organic Chemistry], 17$^{th}$ edition (1973), Hirzel Verlag Stuttgart, p. 261), the conversion of propylene and/or acrolein to acrylonitrile (cf., for example, DE-A 2351151), the conversion of isobutene and/or methacrolein to methacrylonitrile, the oxidative dehydrogenation of hydrocarbons (cf., for example, DE-A 2351151), the conversion of propane to acrylonitrile or to acrolein and/or acrylic acid (cf., for example DE-A 10131297, EP-A 1090684, EP-A 608838, DE-A 10046672, EP-A 529853, WO 01/96270 and DE-A 10028582) etc. The process according to the invention is applicable especially to all of the aforementioned partial oxidations.

The catalysts to be used for such reactions are normally in the solid state.

The catalysts to be used are particularly frequently solid oxide compositions or noble metals (e.g. Ag). In addition to oxygen, the catalytically active oxide composition may contain only one other element or more than one other element (multielement oxide compositions). The catalytically active oxide compositions used are particularly frequently those which include more than one metal, in particular transition metal, element. These are referred to as multimetal oxide compositions.

As a consequence of the generally marked exothermic character of most heterogeneously catalyzed gas phase partial oxidations of organic compounds with molecular oxygen, reaction partners are typically diluted with a gas which is substantially inert under the conditions of the heterogeneously catalyzed gas phase partial oxidation and is capable of absorbing the heat of reaction released with its heat capacity, thus having a favorable effect on the reaction rate.

One of the most frequently used inert diluent gases is molecular nitrogen, which is always used automatically when air is used as a partial oxygen source or exclusively for the heterogeneously catalyzed gas phase partial oxidation.

As a consequence of its general availability, another inert diluent gas which is frequently used is steam. In many cases, cycle gas (which generally also contains oxygen which is yet to be consumed) is also used as an inert diluent gas (cf., for example, EP-A 1180508). Cycle gas refers to the residual gas which remains after a one-stage or multistage (in the multistage heterogeneously catalyzed gas phase partial oxidation of organic compounds, the gas phase partial oxidation, in contrast to the one-stage heterogeneously catalyzed gas phase partial oxidation, is carried out not in one, but rather in at least two, reactors connected in series, in which case oxidants (for example in the form of air) can be supplemented between successive reactors; multiple stages are employed especially when the partial oxidation proceeds in successive steps; in these cases, it is frequently appropriate to optimize both the catalyst and the other reaction conditions to the particular reaction step and to carry out the reaction step in a dedicated reactor, in a separate reaction stage; however, it can also be employed if, for reasons of heat removal or for other reasons (cf., for example, DE-A 19902562), the conversion is spread over a plurality of reactors connected in series; an example of a heterogeneously catalyzed gas phase partial oxidation which is frequently carried out in two stages is the partial oxidation of propylene to acrylic acid; in the first reaction stage, the propylene is oxidized to acrolein and, in the second reaction stage, the acrolein to acrylic acid; correspondingly, the preparation of methacrylic acid (via methacrolein as an intermediate) is usually carried out in two stages starting from isobutene; however, when suitable catalyst charges are used, both aforementioned partial oxidations can also be carried out in one stage (both steps in one reactor); d., for example, EP-A 990636 and EP-A 1106598) heterogeneously catalyzed gas phase partial oxidation of at least one organic compound when the target product is removed more or less selectively (for example by absorption into a suitable solvent; cf., for example, DE-A 19606877) from the product gas mixture. In general, it consists predomionantly of the inert diluent gases used for the partial oxidation, and also of steam typically by-produced in the partial oxidation and carbon oxides formed by undesired complete secondary oxidation. In some cases, it also contains small amounts of oxygen which has not been consumed in the partial oxidation (residual oxygen) and/or unconverted organic starting compounds. Typically, only a portion of the residual gas is used as cycle gas. The remaining amount of residual gas is normally incinerated.

A heterogeneously catalyzed gas phase partial oxidation is normally carried out over a fixed catalyst bed or in a fluidized catalyst bed.

To this end, the starting reaction gas mixture, which consists predominantly of the at least one organic compound to be partially oxidized (typically referred to as precursor compound), molecular oxygen (optionally ammonia in the case of an ammoxidation) and inert diluent gas (including any cycle gas), is generally conducted through the catalyst charge at elevated temperature (generally a few hundred ° C., typically from 100 to 600° C.). The chemical conversion is effected during the contact time on the catalyst surface.

As already mentioned for the cycle gas formation, as a consequence of numerous parallel and subsequent reactions proceeding in the course of the catalytic gas phase partial oxidation, and also as a consequence of the generally used inert diluent gases (under particular conditions, the at least one organic precursor compound can also function as diluent gas, when it is present in excess in the starting reaction gas mixture relative to the molecular oxygen present therein), a heterogeneously catalyzed gas phase partial oxidation does not result in a pure organic target compound being obtained, but rather a reaction gas mixture from which the target product has to be removed.

When the region of the gas phase oxidation forms the actual reaction zone, the product gas mixture, for the purpose of target product removal, is normally fed to what is known as a workup zone in which this removal is effected.

Typically (for example in the case of acrylic acid and in the case of methacrylic acid), the target product removal from the product gas mixture is carried out via extractive, fractionally condensing and/or rectificative separating processes in separating columns containing separating internals, through which the product gas mixture is conducted (cf., for example, DE-A 19606877, DE-A 19631645, EP-A 982289, DE-A 19740253, EP-A 982287, EP-A 1 041 062, EP-A 778 255, EP-A 695 736, DE-A 19 501 325 and EP-A 925 272). The residual gas which remains, as already described, is used, if required, as cycle gas for diluting the starting reaction gas mixture.

To convey the reaction gas mixture through the catalyst charge of the heterogeneously catalyzed partial gas phase oxidation, and also through the downstream workup, a pressure differential is required between reactor inlet and residual gas outlet.

In practice, this pressure differential is typically generated by adjusting the starting reaction gas mixture, before its entry into the oxidation reactor to an elevated pressure compared to the air pressure of the environment. These pressures are typically from 0.2 to 5 bar gauge (bar gauge means elevated pressure compared to normal atmospheric pressure) or more, frequently from 0.5 to 4.5 bar gauge and in many cases from 1 or 2 to 4 bar gauge. High pressures are required in particular when the gas volume to be conveyed is high (for example in the case of high load methods, as described in the document DE-A 19927624, DE-A 19948248, DE-A 19948241, DE-A 19910508, DE-A 10313210, DE-A 10313214, DE-A 10313213 and DE A 19910506), since the latter, for a given reactor and given workup apparatus, also causes an increased pressure drop in the conveyance between the catalyst charge, any intermediate cooler and/or aftercooler charged with random packings, and the workup apparatus.

Since the organic precursor compound to be partially oxidized is in practice frequently stored in liquid form, it is generally sufficient to simply evaporate, in order to bring the organic precursor compound to be partially oxidized to the required reactor inlet pressure. The steam to be used as an inert diluent gas is usually likewise available from highly differing sources with sufficient superatmospheric pressure.

However, this is generally not true for air used as oxygen source (it is typically taken from the atmosphere surrounding the oxidation reactor at atmospheric pressure), the cycle gas (it normally has the reactor inlet pressure minus the pressure drop on the path through the oxidation and through the workup zone) and any other inert diluent gases.

In practice, it is therefore normally necessary to bring at least air used as an oxygen source from a lower starting pressure to a higher final pressure (usually the reactor inlet pressure) by means of a compressor (cf., for example, FIG. 1 of EP-A 990636).

These constituents (for example the oxygen source, air, and the diluent gas source, cycle gas) can be compressed in spatially separated compressors or in a single commpressor (cf. FIG. 1 of EP-A 990636). If required, a plurality of heterogeneously catalyzed gas phase partial oxidation processes can be supplied via an air compressor with compressed air (for example via appropriate feed lines).

The portions of the charging gas mixture (starting reaction gas mixture) which stem from various sources and are substantially at (or brought to) reactor inlet pressure are then, coming from several lines, initially mixed in a, for example static, mixer (generally chambers with internals which generate turbulences), and subsequently optionally heated to inlet temperature and then fed to the oxidation reactor (the entry of the individual gases into the line fed to the static mixer is appropriately selected in such a way (both in sequence and amount) that the formation of explosive mixtures is prevented (in the case of a partial oxidation of propylene to, for example, acrolein and/or acrylic acid, this entry sequence could appropriately be, for example, first cycle gas and/or steam, then crude propene and then air).

In principle, gases could be compressed using compressors of highly differing types. Examples include displacement compressors (for example reciprocating piston compressors, screw compressors and rotary piston compressors), flow compressors (for example turbocompressors, centrifugal compressors, axial compressors and radial compressors) and jet compressors.

Particularly suitable radial compressors are, for example, the Gutehoffnungshütte (GHH) GV10/3L compressor, the Borsig GS900 and GKS450 compressors, the Mannesmann Demag VK80–2 compressor or the Nuovo Pignone SRL1001/B compressor.

The mode of operation of a radial compressor can be illustrated as follows (cf. also DE-A 10259023):

It consists in principle of a housing and at least one rotor which rotates therein, is driven by a drive shapt and is provided with blades. The gas to be compressed enters axially through a suction nozzle. It is deflected radially outward with the centrifugal force of the rotating rotor (closed disk with blades) and thus accelerated to high velocity by the rotor. The function of the housing is to trap the gas and collect it so that it can be further transported through the pressure outlets. The housing simultaneously has the function of converting kinetic energy into pressure. The fact that an increase in cross section reduces the velocity of the gas and thus effects a static pressure increase is generally utilized for this purpose. Various designs of the housing are possible for increasing the cross section. In one-stage compressors or downstream of the last stage of multistage compressors, spiral housings are frequently used. The housing of this type encloses the rotor in spiral form. The cross section increases toward the pressure outlet. The gas flowing through is thus slowed down which implies a simultaneous pressure increase.

Instead of the spiral, it is also possible to use stators, particularly in the case of multistage (e.g. 1- to 3-stage) compressors. The stator is installed in the housing and is in the form of an annular space. It encloses the rotor. Guide blades which form channels with one another which widen continuously in an outward direction are arranged in the stator. In this embodiment, the gas is not accelerated directly into the housing but first flows through the blade channels of the stator. Owing to the widening in the flow direction, they once again produce a decrease in the flow velocity and the consequent pressure build-up.

In multistage compressors, compressed gas (for example air) may advantageously be withdrawn downstream of each compression stage. This then enables, for example, particularly economical compression when the gas to be compressed is required at different pressure levels. The latter is the case, for example, in multistage partial oxidations over the fixed catalyst bed with intermediate air feeding (downstream of the performed oxidation stage) (for example in the two-stage partial oxidation of propylene to acrylic acid). However, it may also be appropriate when a portion of the compressed air is withdrawn in parallel for stripping applications (requires low pressure level).

EP-A 990636 leaves completely open the question of the type of compressor to be used. However, it teaches that the air to be used as an oxygen source merely requires thermal treatment before its compression.

DE-A 10259023 itself considers a thermal treatment of air to be used as an oxygen source to be carried out before the compression not to be necessary. Rather, it is recommended to use a radial compressor as the compressor, since it is said to be largely insensitive toward solid or liquid constituents in the form of very fine particles in the gas to be compressed. This is in particular in view of the fact that when chemical compounds having at least one ethylenically unsaturated double bond ("monomers") are involved in the heterogeneously catalyzed gas phase partial oxidation, the cycle gas generally also contains monomers (in this context, an ethylenically unsaturated double bond refers to a chemical double bond which is between two carbon atoms and, within the molecule, may be either discrete, isolated from other multiple bonds or conjugated or fused to other multiple bonds; a chemical compound having such a double bond is involved in most heterogeneously catalyzed gas phase partial oxidations (for example in virtually all of those cited at the outset); it may, for example, be the organic precursor compound to be partially oxidized (for example butadiene, propylene, isobutene, acrolein, methacrolein), or the target product (for example acrylic acid, methacrylic acid, acrylonitrile, methacrylonitrile) or an intermediate (for example acrolein or methacrolein)). Especially in the case of cocompression of air and cycle gas (according to DE-A 10259023, the compression of the cycle gas and air can be carried out in two separate radial compressors which are driven by two separate motors, or in two compressors which are operated with one motor or in a single compressor which is driven by one motor), polymer particle formation starting from such residual monomers in the course of compression is virtually unavoidable.

However, detailed analyses of long-term experiments have shown that neither the recommendation of DE-A 10259023 nor that of EP-A 990636 is completely satisfactory. Rather, it has been found that, surprisingly, very fine solid and/or liquid particles (having a longest dimension of generally $\leqq 100$ µm, frequently from $\geqq 0.1$ or $\geqq 0.2$ to 50 µm) present in the tiniest amounts in air used as an oxygen source actually have a nonnegligible, adverse effect both in the course of air compression (even when this is carried out together with cycle gas containing residual monomers in one compressor) and in the occurrence of the pressure drop which increases over the operating time when the gas phase partial oxidation is carried out over a fixed catalyst bed. They additionally have an adverse effect on the catalyst performance (activity and/or selectivity).

SUMMARY OF THE INVENTION

It is an object of the present invention to provide a process for operating a continuous heterogeneously catalyzed gas phase partial oxidation of at least one organic compound which substantially remedies the disadvantages of the prior art processes.

We have found that this object is achieved by a process process for operating a continuous heterogeneously catalyzed gas phase partial oxidation of at least one organic compound in an oxidation reactor whose charging gas mixture, in addition to the at least one compound to be partially oxidized and molecular oxygen as the oxidant, comprises at least one diluent gas which is substantially inert under the conditions of the heterogeneously catalyzed gas phase partial oxidation, by using air, both as the oxygen source and the inert gas source for the charging gas composition, which has been compressed beforehand in a compressor from a low staring pressure to a higher final pressure, which comprises subjecting the air, before its entry into the compressor, to at least one mechanical separating operation by which the solid particles dispersed in the air can be removed.

DETAILED DESCRIPTION OF THE PREFERRED EMBODIMENTS

In air cleaning processes which employ a mechanical separating operation and are suitable in accordance with the invention, external forces normally generate movement of the dispersed solid particles (and/or liquid particles) relative to the carrier gas. Depending on the main forces acting, a distinction is drawn, for example, between the following separation principles:

impingement, impactive and centrifugal forces in deflection separators,
centrifugal forces in centrifugal separators,
impactive action and adhesive forces in filtering separators,
electrostatic forces in electrofilters.

In other words, gas cleaning apparatus which employs a mechanical separating operation and is suitable in accordance with the invention is, for example, chamber, impingement and centrifugal separators which utilize gravitational forces. However, acoustic separators can also be employed for the process according to the invention. Preference is given to aerocyclones. In a simple manner, the mechanical separating operation used in accordance with the invention may also be filtering.

Useful filter layers are, for example, filter fabric, porous filter compositions, paper web or oil-wetted metal filters. Electrostatic separators can also be employed in accordance with the invention. In the simplest manner, the air to be filtered can also flow through an inert fixed bed in which the very fine solid (and/or liquid) particles present in the air separate before the air reaches the compressor. In this document, the definition of the mechanical separating operation is also intended to include spray apparatus in which the air is exposed to liquid droplets in occurrent or countercurrent (for example of high-boiling organic liquids or of water) which are capable of absorbing solid particles present in the air. The spray liquid is exchanged after a few recirculations, in order to prevent such aeration with solid particles. At the end of the washing, it is appropriate to attach a droplet separator.

It will be appreciated that different mechanical separating operations connected in series can also be employed in accordance with the invention.

A mechanical separating operation which is preferred in accordance with the invention is filtering: this allows particles having a longest dimension of 0.001 μm and less to be retained in a comparatively simple manner. When the filter material is dimensioned and selected in an appropriate manner, it is possible to achieve degrees of separation of more than 99.9% in a substantially less expensive manner than in the case of electrostatic filters.

The separating action in filtering is based substantially on impingement action (impact tion of very fine particles on the filter element) and diffusion, although other factors such as gravity and electrostatic forces also have an influence. Although the filtration is not a pure sieving procedure (surprisingly, the particles separated by filtration in the process according to the invention are frequently substantially smaller than the pores of the filter medium), narrow-mesh filters have a higher degree of efficacy in the process according to the invention than wide mesh filters, although at the cost of resistance, i.e. economic viability.

It is appropriate from an application point of view to use fabric filters, among other filters, for the process according to the invention. Suitable in principle for the process according to the invention are filter fabrics made of natural or synthetic fibers. In other words, both filter fabrics made of PVC, polyamides (Perlon®, Nylon®), wool, polyacrylonitrile (Redon®, Dralon®), polyesters and polytetrafluoroethylene (Teflon®), and siliconized glass fabric are suitable in accordance with the invention. According to the invention, random fiber webs of the same materials can also be used instead of the fabrics. They usually consist of synthetic fibers which are applied to a support fabric with the aid of a needle process (for example polyester fibers on a polyester gauze) or secured with binders. However, filter fabric which can be used in accordance with the invention is also cotton or linen. Useful material for air filters also includes wire knits, mats made of metal turnings, glass or chemical fibers, asbestos or paper. For better filtering, the filter fabric is generally compacted toward the clean air side. Generally suitable for the process according to the invention are filters as used in large air conditioning and ventilation units. Preference is given to a favorable fire performance of the material in the context of DIN 53438.

The most important requirement for the filter fabric (filter cloth) or fiber web suitable for the process according to the invention is a very high air permeability coupled with high retention capability.

The superficial velocity of gas to be filtered in the process according to the invention should typically be from 5 to 20000 $m^3$ (STP)/$m^2$·h, frequently from 500 or 1000 to 15000 $m^3$ (STP)/$m^2$·h. Preference is given in accordance with the invention to superficial velocities of from 2000 to 10000 $m^3$ (STP)/$m^2$·h.

The pressure drop (difference between the pressure of the gas to be filtered upstream of the filter and the pressure of the gas to be filtered after passing through the filter), at a superficial velocity of 5000 $m^3$ (STP)/$m^2$·h, should, appropriately in accordance with the invention, for fresh fabric, be from about 0.01 to 10 mbar, preferably from 0.05 or 0.1 to 5 mbar, more preferably from 0.2 to 1 mbar. At the same time, the degree of separation should be at least 75% or 85% or 95%, preferably at least 97% and more preferably at least 99%.

Typically, the filter fabric or web will be replaced by new fabric or web (or passed to its cleaning) at the latest when the pressure drop at the aforementioned superficial velocity has risen by 10 mbar, preferably only by 5 mbar, more preferably only by 2 mbar.

The rate at which the air, for example aspirated by a radial compressor, flows to the filter fabric or web in the process according to the invention is frequently from 0.5 to 3 m/s.

It is essential to the invention that the filter fabric or web does not significantly stretch under the superficial velocity of gas to be filtered.

In addition, the stretching of the filter fabric or web in the temperature range from about −30° C. to +50° C. (typical possible external temperatures) should not change significantly. In particular, the filter fabric or web should not become brittle at the possible low external temperatures.

It has been found that filter webs which are particularly favorable in accordance with the invention are those which are made of polyester fibers needled to polyester gauze and, at a superficial velocity of 5000 $m^3$ (STP)$_m^2$·h and a pressure drop of from 0.1 to 5 mbar in the fresh state, achieve the degrees of separation according to DIN EN 779 (filter class G3). These may be, for example.

| Particle size | Degree of separation (% based on the total of particles of the particular particle size) |
|---|---|
| ≦0.5 μm | 0–5% |
| ≧0.5 and ≦1 μm | 15–35% |
| ≧1 and ≦3 μm | 30–55% |
| ≧3 and ≦5 μm | 60–90% |
| ≧5 and ≦10 μm | 85–98% |
| ≧10 μm | 98–100% |

All of the aforementioned properties are fulfilled, for example, by filter web of the FIBROBAND® brand, of the filter class G 3 (DIN EN 779) from GEA Delbag Luftfilter GmbH.

One possible embodiment of fabric or web filters for the process according to the invention is bag filters, for example in series or parallel design. The aspirated or blown-in crude gas (according to the invention, normally the air) generally enters the bags from below, passes through the filter fabric (cloth), deposits the very fine particles present therein on the fabric and leaves the filter at the top as clean gas.

A more space-saving design is what is known as a flat filter. The dust is retained in filter bags which consist of frames covered with filter cloth.

The cleaning of used filter fabric can be carried out, for example, by compressed air flowing in the opposite sense and/or by vibration. Instead of cleaning, the fabric can be replaced by fresh fabric.

In a particularly advantageous manner from an application point of view, an embodiment as a fully automated roll belt filter will be selected for the process according to the invention (for example according to FIG. 4 in Ullmanns Encyklopädie der technischen Chemie [Ullmann's Encyclopedia of Industrial Chemistry] $4^{th}$ edition, Verlag Chemie (Weinheim), Vol. 2 (Verfahrenstechnik I [Process Technology I]), 1972, p. 238. When an adjustable pressure drop rise has been attained (generally from 0.05 to 10 mbar or from 0.1 to 5 mbar), the motor drive is activated via a pressure differential control and sufficient filter belt is supplied that the target value of the pressure drop (for example that corresponding to fresh filter belt) has been attained again.

In one possible embodiment, the roll belt filter can also be operated in a steady-state manner, i.e. fresh filter belt is supplied continuously at a low rate. Instead of supplying fresh filter belt under pressure drop control, the roll belt filter can also be supplied under time control (for example every 1–3 days).

Alternatively, filter candles can also be used for the process according to the invention. These are usually filter elements made of porous, ceramic, metallic or plastics moldings. These filter elements (candles) are cylinders which are closed on one side and sealed at the open end in the bottom of the apparatus accommodating them. The air flows through this hollow cylinder from the outside inward and is thus purified.

Appropriately, the air filtration in the process according to the invention is carried out in a plurality of stages (for example two stages). Useful filter types for the first filtration stage are in particular the following filter types: flat filters (for example roll belt filters), cassette filters (rectangular filter element), cartridge filters (cylindrical filter element) and bag filters (bag-shaped filter element in rectangular frame).

For the second filtering stage, useful filters are in particular bag filters and cassette filters.

In the higher filtering stages, higher filter classes ("finer filters") are appropriately used. A favorable combination would be, for example, a bag filter for the first stage and a cassette filter for the second stage. A further possible combination is a roll belt filter in the first filtering stage and a bag filter or cassette filter for the second filtering stage.

A suitable combination for a two-stage air filtration is also the pairing of a filter of the GAE YTS Roll type (Manufacturer: Airguard Industries) for the first filtering stage and a filter of the Koch Multicell 95-K9242412 (Manufacturer: Koch Filter Company) for the second filtering stage.

Preference is given in accordance with the invention to the filter classes F6 (lower filter class) to F9 (higher filter class) according to DIN EN 779 and/or ASHRAE 52.1.

Oil-wetted metal filters are also suitable in accordance with the invention. Especially suitable for the process according to the invention is, for example, a rotary filter with oil-wetted metal filter cells. The filter cells are circulated continuously in a patemoster-like manner by a motor drive. When the cells circulate, they are conducted through a cleaning vessel and constantly purified and newly wetted here.

According to the invention, the air is normally filtered alone. However, it will be appreciated that the air can also be filtered together with cycle gas.

The latter is appropriate in particular when air and cycle gas are compressed in one and the same compressor.

However, practice has shown that filtering of the cycle gas is not indispensible, i.e. generally not necessary.

If required, filters can also be used for the process according to the invention which, at the same time or connected downstream, are suitable for separating mists, i.e. substances which are present in the form of droplets, i.e. liquid, in the gas (for example in the air). After the impingement on the filter material, the mists normally agglomerate in order to subsequently flow out of the filters. Correspondingly constructed bag filters or candle filters may also find use.

However, a content of liquid droplets in the gas to be filtered (for example the air) normally leads to fouling of, for example, the filter fabric.

It is therefore appropriate in accordance with the invention when the temperature of the gas to be filtered (for example of the air) is not at the dewpoint.

It is preferably at least 30° C. above the dewpoint.

In order to ensure the latter, the gas to be filtered, which is fed to the compressor or aspirated by it, before it is filtered, is appropriately conducted through a heating register and appropriately heated.

In the simplest manner, such a heating register consists of a network of pipes conducting hot steam. However, it could alternatively consist of an electrically heated wire braid. It is also possible in principle to use indirect heat exchangers of any type for this purpose (for example tube bundle heat exchangers).

In order to prevent damage to the filtering and/or heating apparatus by coarse aspirated material, it is appropriate to position a coarse-mesh screen upstream of it, which has an appropriate repulsive action.

When the gas phase partial oxidation is a partial oxidation performed in multiple stages, and compressed secondary air has to be added to the reaction mixture between the individual stages, it is advantageous likewise to apply the process according to the invention to this air.

Advantageously in accordance with the invention, primary air to be added to the starting reaction gas mixture and secondary air to be added to the reaction gas mixture between the stages will be compressed together and subjected together to the inventive mechanical separating operation.

It is surprising that the advantageous effects of the procedure according to the invention can be detected even when the contents of very fine solid particles in the air used in the starting reaction gas mixture is $\leq 150$ mg/m$^3$, or $\leq 100$ mg/m$^3$, or $\leq 50$ mg/m$^3$. The investigations which have been carried out have shown that the content of such very find solid particles in air is generally $\geq 10$ mg/m$^3$.

The process according to the invention is significant in particular for what are known as high-load processes in which the hourly space velocity of starting reaction gas mixture (charging gas mixture) on the catalyst charge (especially in the case of a fixed bed charge) is increased; in these processes, an increased amount of starting reaction gas mixture, and thus an increased amount of compressed air, per unit time are conducted through the reactor and the catalyst charge.

This means that the process according to the invention is particularly advantageous for continuous heterogeneously catalyzed gas phase partial oxidations of at least one organic compound in which the hourly space velocity of the at least one organic compound on the catalyst charge is $\geq 120$ l (STP)/l of catalyst charge·h (normal loading extends from 60 to <120 l (STP)/l·h), or $\geq 130$ l (STP)/l·h, or $\geq 135$ l (STP)/l·h, or $\geq 140$ l (STP)/l·h, or $\geq 150$ l (STP)/l·h, or $\geq 160$ l (STP)/l·h. In general, the aforementioned catalyst hourly space velocity will be $\leq 600$ l (STP)/l·h, frequently $\leq 400$ l (STP)/l·h or $\leq 350$ l (STP)/l·h, or $\leq 300$ l (STP)/l·h, or $\leq 250$ l (STP)/l·h and sometimes $\leq 200$ l (STP)/l·h.

The aforementioned is especially true when the gas phase partial oxidation is the partial oxidation of propene to acrolein or the gas phase partial oxidation of acrolein to acrylic add (correspondingly, the aforementioned catalyst hourly space velocities are the propene or acrolein hourly space velocity).

These high-load partial oxidations can otherwise be carried out as described in documents DE-A4 431 957, DE-A 4 431 949, DE-A 19 948 241, DE-A 19 910 506, WO 00/53556, EP-A 1 106 598, DE-A 19 910 508, WO 00/53559, WO 00/63558, WO 00/53557 and DEA 19 948 248.

The reactors used are normally tube bundle reactors.

The starting reaction gas mixture of the propane gas phase partial oxidation typically has the following composition (volume (l(STP) ratio):

propane:oxygen:inert gases (including steam)=
1:(1.0 to 3.0):(5 to 25).

The starting reaction gas mixture of the acrolein gas phase partial oxidation typically has the following composition (volume (l(STP)) ratio);

acrolein:oxygen:steam:inert gases=
1:(1 to 3):(0 to 20):(3 to 30).

EXAMPLE AND COMPARATIVE EXAMPLE

A) General Description of the Production Plant

The example and the comparative example were carried out in a production plant for preparing acrylic acid which is illustrated by the process of EP-A 784 046. It consists of three parallel production lines of which each comprises two multitube reactors connected in series. The first reactor serves in each case for partial oxidation of propene to acrolein, the second for partial oxidation of acrolein to acrylic acid.

The acrylic acid-containing reaction gases which left the second reactors were combined and absorbed in an absorption column with a mixture of Diphyl® and dimethyl phthalate in accordance with DE-A 19 606 877. A portion of the reaction gas (cycle gas) which had been virtually freed of acrylic acid by washing and consisted mainly of nitrogen was recycled as a constituent of the charging gas mixture for the first reactors, while the remaining portion was disposed of. The liquid effluent withdrawn from the absorption column which consisted predominantly of the absorbent and acrylic acid was fed to its further workup.

The propene used was propene of chemical grade quality. It contained $\geq 95.0$ mol % of propene and $\geq 4$ mol % of propane and was withdrawn in gaseous form from a line. The reaction gas mixture leaving the first reactors was cooled and conducted into the second reactors with the addition of secondary air.

The primary air required for the starting reaction gas mixture and the secondary air required were aspirated from the environment together using a turbo radial compressor (manufacturer GHH, model GV 10/3) and fed to the process at a pressure of 2.5 bar. A heating register (heated with 4 bar of steam) heated the air before its compression to 35° C. The cycle gas was compressed and conveyed using a separate radial compressor from the manufacturer GHH, model GV 10/3.

The reactors were tube bundle reactors of the type described in the documents EP-A 700 893 and EP-A 700 714.

The first reactors contained a few thousand tubes (cooled with molten salt, salt bath temperature approx. 290° C.), as did the second reactors (cooled with molten salt, salt bath temperature approx. 260° C.).

The first reactors were charged with an unsupported catalyst in accordance with Example 1 of DE-A 10 046 957 and the second reactors were charged with a coated catalyst in accordance with preparation example 5 of DE-A 10 046 928 (stoichiometry: $Mo_{12}V_3W_{1.2}Cu_{2.4}O_x$).

The plant was operated in such a way that 17 t of acrylic acid were generated per hour.

The composition of the charging gas mixture from the first reactors was;
from 6 to 6.5% by volume of chem. grade propene,
from 3 to 3.5% by volume of $H_2O$,
from 0.3 to 0.5% by volume of CO,
from 0.8 to 1.2% by volume of $CO_2$
from 0.01 to 0.04% by volume of acrolein,
from 10.4 to 10.7% by volume of $O_2$ and, as
the remainder ad 100%, molecular nitrogen.

The amount of air required for the starting reaction gas mixture fed to the first reactors was 44000 $m^3$ (STP)/h. The amount of secondary air required for the second reactors was 12000 $m^3$ (STP)/h. The total amount of air to be compressed was thus 56 000 $m^3$ (STP)/h.

Under these conditions, the production plant was in each case operated for eleven months with the following variations:

B) Example

Downstream of the heating register was also disposed, upstream of the compressor, a roll belt filter. The (regeneratable) filter material was a filter mat from GEA Delbag Luftfilter GmbH (Berlin), brand name FIBROBAND, filter class G3 (DIN EN 779).

The filter material consisted of randomly layered polyester fibers on a rigid, tear-resistant polyester gauze. The filter surface area was 10.8 $m^2$ (breadth 2.74 m; height 3.95 m).

The properties of the filter material were such that, as a function of the volume flow rate V, in the fresh state, gave the following pressure drops ΔP:

| V [$m^3$ (STP)/h$m^2$] | ΔP [mbar] |
|---|---|
| 2000 | 0.1 |
| 3000 | 0.15 |
| 4000 | 0.22 |
| 5000 | 0.31 |
| 6000 | 0.42 |

The dust storage capability was approx. 400 g/$m^2$.

The roll belt was controlled via a pressure drop measurement.

As soon as the pressure drop had attained a value of 3 mbar, the filter belt was rolled on until the pressure drop was only 2 mbar (only a portion of the filter surface was thus replaced by fresh surface, which reduces the total consumption of filter material).

The average degree of deposition was 88.1%.

No rotor vibrations could be observed in the radial compressor.

C) Comparative Example

There was free air access to the radial compressor which was screened by a large-mesh sieve for safety reasons only. At the end of the experimental period, uneven running and shaft vibrations could be observed in the radial compressor. The pressure drop in the reactors rose more sharply than in B). The selectivity of acrylic acid formation fell slightly.

U.S. Provisional patent application No. 60/492,726, filed on Aug. 6, 2003 and U.S. provisional patent application No. 60/530,616, filed on Dec. 19, 2003, are included in the present application by literature reference With regard to the abovementioned teaching, numerous modifications and deviations from the present invention are possible. It may therefore be assumed that the invention, within the scope of the appended claims may be performed in a different way to that specifically described herein.

We claim:

1. A process for operating a continuous heterogeneously catalyzed gas phase partial oxidation of at least one organic compound selected from the group consisting of chemical compounds having an ethylenically unsaturated double bond, isobutane and propane in an oxidation reactor whose charging gas mixture, in addition to the at least one compound to be partially oxidized and molecular oxygen as the oxidant, comprises at least one diluent gas which is substantially inert under the conditions of the heterogeneously catalyzed gas phase partial oxidation, by using air, both as the oxygen source and the inert gas source for the charging gas composition, which has been compressed beforehand in a compressor from a low starting pressure to a higher final pressure, which comprises subjecting the air, before its entry into the compressor, to at least one mechanical separating operation by which the solid particles dispersed in the air can be removed.

2. The process as claimed in claim 1, which is conducted over a fixed catalyst bed.

3. The process as claimed in claim 1, which is conducted at a pressure 0.2 to 5 bar above atmospheric pressure.

4. The process as claimed in claim 1, wherein the air is compressed by means of a radial compressor.

5. The process as claimed in claim 1, wherein the at least one organic compound is at least one chemical compound having an ethylenically unsaturated double bond which is selected from the group consisting of propene, acrolein, iso-butene and methacrolein.

6. The process as claimed in claim 1, wherein the mechanical separating operation employed is a filtration.

7. The process as claimed in claim 6, wherein the filtration operation employs a filter of a filter fabric or a fiber web.

8. The process as claimed in claim 7, wherein the filter is a fiber web based on a polyester.

9. The process as claimed in claim 8, wherein the filter is a roll belt filter.

10. The process as claimed in claim 8, wherein the filter is a bag filter.

11. The process as claimed in claim 6, wherein, when the filter is fresh, the filtration operation experiences a pressure drop ranging from 0.01 to 10 mbar at a superficial velocity of 5000 $m^3$ (STP)/$m^2 \cdot h$.

12. The process as claimed in claim 6, wherein the air is conducted through a heating apparatus before the filtration operation.

13. The process as claimed in claim 1, wherein the continuous heterogeneously catalyzed gas phase partial oxidation of at least one organic compound is one in which the hourly space velocity of the at least one organic compound on the catalyst charge is $\geq 120$ l (STP)/l·h.

14. The process as claimed in claim 13, wherein said hourly space velocity of the at least one organic compound on the catalyst charge is $\geq 130$ l (STP)/l·h.

15. The process as claimed in, claim 14 wherein said hourly space velocity of the at least one organic compound on the catalyst charge is $\geq 140$ l (STP)/l·h.

16. The process as claimed in claim 1, wherein the mechanical separating operation is a separation in a cyclone.

17. The process as claimed in claim 3, which is conducted at a pressure 0.5 to 4.5 bar above atmospheric pressure.

18. The process as claimed in claim 17, which is conducted at a pressure 1 to 4 bar above atmospheric pressure.

19. The process as claimed in claim 18, which is conducted at a pressure 2 to 4 bar above atmospheric pressure.

20. The process as claimed in claim 1, wherein the filtration of air is conducted in at least 2 stages.

21. The process as claimed in claim 1, wherein the gas phase reaction is conducted in a plurality of oxidation stages, whereby secondary air is compressed and added to the reaction mixture between the individual oxidation stages.

22. The process as claimed in claim 1, wherein the filtration of air is not conducted at the dewpoint of the air that is employed.

23. The process as claimed in claim 5, wherein the at least one organic compound is acrolein.

24. The process as claimed in claim 1, wherein the charging gas mixture has the following composition:
   propene:oxygen:inert gases (including steam)=1:(1.0 to 3.0):(5 to 25).

25. The process as claimed in claim 1, wherein the charging gas mixture has the following composition:
   acrolein:oxygen:steam:inert gases=1:(1.0 to 3.0):(0 to 20):(3 to 30).

26. The process as claimed in claim 1, wherein the air obtained from the oxidation reaction is recycled and filtered with air in the mechanical separating operation.

* * * * *